United States Patent [19]  [11] 4,371,526
Rovnyak  [45] Feb. 1, 1983

[54] PHOSPHINYLALKANOYL SUBSTITUTED 4,5-DIHYDROPYRAZOLE-5-CARBOXYLIC ACID DERIVATIVES AND HYPOTENSIVE METHOD AND COMPOSITION

[75] Inventor: George C. Rovnyak, Hopewell, N.J.

[73] Assignee: E. R. Squibb & Sons, Inc., Princeton, N.J.

[21] Appl. No.: 294,944

[22] Filed: Aug. 21, 1981

[51] Int. Cl.³ ............... A61K 31/675; A61K 31/685; C07F 9/58; C07F 9/65
[52] U.S. Cl. .................................. 424/200; 424/199; 548/112; 546/22
[58] Field of Search ............... 548/112; 546/22; 424/200, 199

[56] References Cited

U.S. PATENT DOCUMENTS

| 4,105,776 | 8/1978 | Ondetti et al. | 424/274 |
| 4,151,172 | 4/1979 | Ondetti et al. | 424/274 |
| 4,168,267 | 9/1979 | Petrillo | 424/274 |
| 4,211,786 | 7/1980 | Rovnyak | 424/273 P |
| 4,254,267 | 3/1981 | Rovnyak | 548/379 |
| 4,266,065 | 5/1981 | Rovnyak | 548/379 |

Primary Examiner—John M. Ford
Assistant Examiner—Natalia Harkaway
Attorney, Agent, or Firm—Lawrence S. Levinson; Stephen B. Davis

[57] ABSTRACT

Compounds of the formula

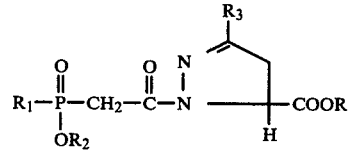

are disclosed. These compounds are useful as hypotensive agents due to their angiotensin converting enzyme inhibition activity.

12 Claims, No Drawings

PHOSPHINYLALKANOYL SUBSTITUTED 4,5-DIHYDROPYRAZOLE-5-CARBOXYLIC ACID DERIVATIVES AND HYPOTENSIVE METHOD AND COMPOSITION

BACKGROUND OF THE INVENTION

Petrillo in U.S. Pat. No. 4,168,267 discloses that phosphinylalkanoyl substituted prolines are useful as hypotensive agents due to their angiotensin converting enzyme inhibition activity.

Petrillo in U.S. patent application Ser. No. 212,911 filed Dec. 4, 1980, now U.S. Pat. No. 4,337,201, discloses that various acyloxyalkanoyl esters of phosphinylalkanoyl proline and substituted prolines are useful hypotensive agents due to their angiotensin converting enzyme inhibition activity.

Rovnyak in U.S. Pat. Nos. 4,211,786; 4,254,267; and 4,266,065 disclose that mercaptoalkanoyl derivatives of 4,5-dihydropyrazole-5-carboxylic acid, wherein the dihydropyrazole ring can also be substituted in the 3-position by an aryl, heteroaryl, or alkyl group, are also useful as hypotensive agents due to their angiotensin converting enzyme inhibition activity.

Ondetti et al. in U.S. Pat. No. 4,105,776 disclose the mercaptoalkanoyl derivatives of proline are useful hypotensive agents due to their angiotensin converting enzyme inhibition activity.

SUMMARY OF THE INVENTION

This invention is directed to phosphinylalkanoyl substituted 4,5-dihydropyrazole-5-carboxylic acid compounds of the formula (I)

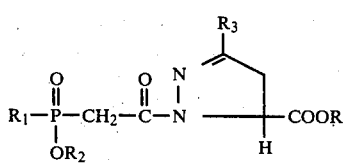

and salts thereof.

R and $R_2$ are independently selected from hydrogen, lower alkyl of 1 to 4 carbons, benzyl, and

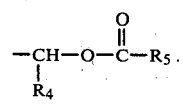

$R_3$ is hydrogen, alkyl,

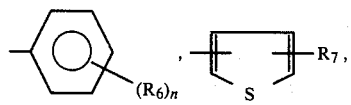

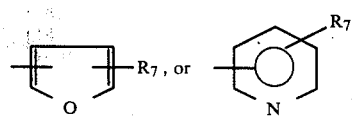

$R_1$ is alkyl or

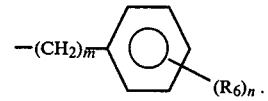

$R_4$ is hydrogen, lower alkyl of 1 to 4 carbons, phenyl, or

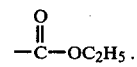

$R_5$ is hydrogen, lower alkyl of 1 to 4 carbons, lower alkoxy of 1 to 4 carbons, phenyl, or $R_4$ and $R_5$ taken together are $-(CH_2)_2-$, $-(CH_2)_3-$, $-CH=CH-$, or

$R_6$ is hydrogen, lower alkyl of 1 to 4 carbons, lower alkoxy of 1 to 4 carbons, lower alkylthio of 1 to 4 carbons, chloro, bromo, fluoro, trifluoromethyl or hydroxy.

n is 1, 2, or 3 provided that n is 2 or 3 only when $R_6$ is hydrogen, methyl, methoxy, chloro, or fluoro.

$R_7$ is hydrogen, lower alkyl of 1 to 4 carbons, chloro, bromo, or fluoro.

m is zero or an integer from 1 to 8.

DETAILED DESCRIPTION OF THE INVENTION

This invention in its broadest aspects relates to the phosphinylalkanoyl substituted 4,5-dihydropyrazole-5-carboxylic acid compounds of formula I above, to compositions containing such compounds and to the method of using such compounds as hypotensive agents.

The term alkyl used in defining $R_1$ and $R_3$ refers to straight or branched chain radicals having up to eight carbons, for example methyl, ethyl, propyl, isopropyl, butyl, isobutyl, t-butyl, pentyl, isopentyl, heptyl, octyl, etc. The term lower alkyl used in defining various symbols refers to straight or branched chain radicals having up to four carbons with methyl and ethyl being preferred. Similarly, the terms lower alkoxy and lower alkylthio refer to such lower alkyl groups attached to an oxygen or sulfur.

The symbols

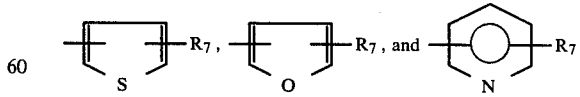

represent that the thienyl or furyl group is attached at the 2- or 3-position and that the pyridyl is attached at either the 2-, 3- or 4-position. The $R_7$ group is, of course, attached to any available carbon atom.

The compounds of formula I can be prepared by coupling a phosphinate of the formula (II)

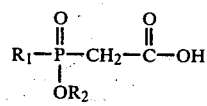

wherein $R_2$ is lower alkyl or benzyl with a dihydropyrazole of the formula (III)

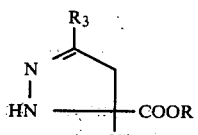

wherein R is hydrogen, lower alkyl or benzyl. The reaction is performed in the presence of a coupling agent such as 1,1-carbonyldiimidazole or dicyclohexylcarbodiimide and in an aprotic solvent such as tetrahydrofuran or acetonitrile.

The $R_2$ and/or R ester group can be removed to yield the diacid (i.e. both $R_2$ and R are hydrogen) by treatment with a cleaving agent such as bromotrimethylsilane in the case of the phosphinic acid alkyl ester or by hydrogenation with palladium and carbon catalyst in the case of the benzyl ester.

The ester products of formula I wherein R is

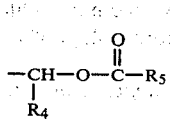

can be obtained by treating the monoester product of formula I wherein R is hydrogen and $R_2$ is alkyl or benzyl with a compound of the formula (IV)

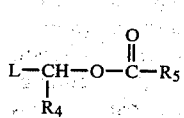

wherein L is a leaving group such as chlorine, bromine, tolylsulfonyloxy, etc., followed by removal of the $R_2$ ester group as described above. This reaction is performed in dimethylformamide containing a base such as triethylamine or potassium carbonate or potassium fluoride.

The diester products of formula I wherein $R_2$ and R are the same and are

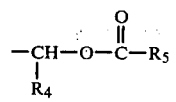

can be obtained by treating the product of formula I wherein $R_2$ and R are both hydrogen or an alkali metal salt with two or more equivalents of the compound of formula IV.

Similarly, the ester products of formula I wherein $R_2$ is

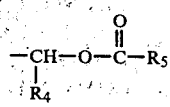

can be obtained by treating the monoester of formula I wherein $R_2$ is hydrogen and R is benzyl with the compound of formula IV followed by removal of the R ester group as described above.

Also, the diacid products of formula I can be obtained by coupling the phosphinate of formula II wherein $R_2$ is hydrogen with the dihydropyrazole of formula III wherein R is hydrogen. However, the two step procedure described above is preferred.

The phosphinate of formula II can be prepared as described by Petrillo in U.S. Pat. No. 4,168,267 at col. 2, line 37 to col. 4, line 25.

The 4,5-dihydropyrazole-5-carboxylic acids of formula III wherein $R_3$ is phenyl or substituted phenyl are prepared as described by Rovnyak in U.S. Pat. No. 4,211,786 at col. 4, lines 46 to 53. Those wherein $R_3$ is substituted or unsubstituted thienyl, furyl, or pyridyl are prepared as described by Rovnyak in U.S. Pat. No. 4,254,267 at col. 5, line 64 to col. 6, line 36 and those wherein $R_3$ is hydrogen or alkyl are prepared as described by Rovnyak in U.S. Pat. No. 4,266,065 at col. 5, line 60 to col. 6, line 20 and in the representative examples in these patents. Of course, the 3-substituted or unsubstituted 4,5-dihydropyrazole-5-carboxylic acid can be converted to the ester by conventional esterification procedures, for example when R is benzyl the acid is treated with benzyl alcohol and an acid catalyst such as sulfuric acid or thionyl chloride.

The reactants of formula IV wherein $R_5$ is other than lower alkoxy are prepared from aldehydes and acid halides according to known literature methods. [J. Amer. Chem. Soc., Vol. 40, p. 1732 (1918); J. Amer. Chem. Soc., Vol. 43, p. 651, 660 (1921); Acta. Chem. Scand., Vol. 20, p. 1273 (1966)]. Compounds of formula IV wherein $R_5$ is lower alkoxy are prepared by α-chlorination of alkyl chloroformates (gaseous chlorine and light or sulfuryl chloride and dibenzoylperoxide) and treatment of the products thus formed with an alcohol according to known literature methods [Compt. rend, Vol. 169, p. 1074 (1919) and British Pat. No. 1,426,717].

The starting materials of formula III and the products of formula I contain an asymmetric carbon (i.e., the carbon to which the —COOR group is bonded) and accordingly exist in stereoisomeric forms or as the racemic mixture thereof. The above described synthesis of the compounds of formula I can utilize the racemate or one of the enantiomers of the starting material of formula III. It is believed that the activity of the racemic product is due mostly to the S-isomer, and this isomer is accordingly preferred. The stereoisomers of the starting materials of formula III can be separated by conventional fractional crystallization of the diastereomeric salt mixture formed with an optically active amine such as α-methylbenzylamine.

The compounds of this invention wherein at least one of R or $R_2$ is hydrogen, form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product. The salts are formed using conventional techniques.

Preferred compounds of this invention are the compounds of formula I wherein:

R and $R_2$ are independently selected from the group consisting of hydrogen, alkali metal, and $$-\underset{R_4}{\underset{|}{CH}}-O-\underset{\underset{O}{\|}}{C}-R_5$$

provided that at least one of R and $R_2$ is hydrogen or an alkali metal.

$R_3$ is $$-\!\!\!\left\langle\!\!\!\bigcirc\!\!\!\right\rangle\!\!-R_6.$$

$R_4$ is hydrogen, methyl, or $$-\underset{\underset{O}{\|}}{C}-OC_2H_5.$$

$R_5$ is lower alkyl of 1 to 4 carbons or phenyl.

$R_6$ is hydrogen, methyl, methoxy, methylthio, trifluoromethyl, chloro, bromo, fluoro, or hydroxy.

$R_1$ is alkyl or $$-(CH_2)_{\overline{m}}\!\!\left\langle\!\!\!\bigcirc\!\!\!\right\rangle\!\!-R_6$$

wherein $R_6$ is as defined above and m is an integer from 2 to 6.

Most preferred are the compounds of formula I wherein

R and $R_2$ are independently selected from the group consisting of hydrogen, alkali metal, $$-\underset{\underset{CO_2C_2H_5}{|}}{CH}-O-\underset{\underset{O}{\|}}{C}-C(CH_3)_3, \quad -\underset{\underset{CH_3}{|}}{CH}-O-\underset{\underset{O}{\|}}{C}-CH_3,$$

and $$-CH_2-O-\underset{\underset{O}{\|}}{C}-C(CH_3)_3$$

provided that at least one of R and $R_2$ is hydrogen or alkali metal.

$R_3$ is phenyl.

$R_1$ is $$-(CH_2)_4\!\!\left\langle\!\!\!\bigcirc\!\!\!\right\rangle\!\!.$$

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

(+)-4,5-Dihydro-1-[[hydroxy(4-phenylbutyl)-phosphinyl]acetyl]-3-phenyl-1H-pyrazole-5-carboxylic acid (a) (+)-4,5-Dihydro-3-phenyl-1H-pyrazole-5-carboxylic acid A mixture of 10.0 g. of 3-benzoylacroylic acid, 1.8 g. of hydrazine, and 3.7 g. of potassium hydroxide in 30 ml. of aqueous ethanol (1:1) is stirred and heated at reflux for 2 hours. The cooled solution is treated with 5 ml. of concentrated hydrochloric acid to pH 4.0 to precipitate 7.1 g. of solid, m.p. 180°–182°. This material is dissolved in 40 ml. of warm dimethylformamide and treated with 140 ml. of methanol to crystallize 3.9 g. of (±)-4,5-dihydro-3-phenyl-1H-pyrazole-5-carboxylic acid, m.p. 199°–201°.

Anal. calc'd. for $C_{10}H_{10}N_2O_2$: C, 63.14; H, 5.29; N, 14.73, Found: C, 63.06; H, 5.40; N, 14.71.

A solution of 66.2 g. of the above racemic amino acid dissolved in 125 ml. of warm dimethylsulfoxide is treated with 42.2 g. of d-(+)α-methylbenzylamine. Dilution of this solution with 480 ml. of acetonitrile gives 83.1 g. of solids, m.p. 152°–154°; $[\alpha]_D^{20} = +29°$ (1% in methanol). Two recrystallizations from methanol give 29.1 g. of material, m.p. 177°–179°; $[\alpha]_D^{20} = +205°$ (1% in methanol).

The above salt (29.1 g.) is dissolved in 100 ml. of water containing 3.7 g. of sodium hydroxide and washed twice with ethyl acetate. The aqueous solution is treated with 6 N hydrochloric acid to pH 4.0 to precipitate 16.5 g. of nearly colorless solid (+)-4,5-dihydro-3-phenyl-1H-pyrazole-5-carboxylic acid, m.p. 294°–296°; $[\alpha]_D^{20} = +235°$ (1% in methanol).

(b) [Ethoxy(4-phenylbutyl)phosphinyl]acetic acid

A solution of 36.4 g. of 1-chloro-4-phenylbutane in 100 ml. of ether is added dropwise to a slurry of 4.8 g. magnesium metal in 50 ml. of ether at a rate sufficient to maintain gentle reflux, followed by stirring for one hour. After cooling and filtration under argon, the original solution is added dropwise to a chilled (0°) solution of 25.7 g. of diethyl chlorophosphite in 100 ml. of ether at a rate to maintain the temperature at 0°–10°. The mixture is then heated at reflux temperature for 1.5 hours. After filtration and concentration at atmospheric pressure, under argon, the residue is distilled in vacuo to give 29.7 g. of (4-phenylbutyl)phosphonous acid, diethyl ester, b.p. 110°–113°/0.1 mm of Hg.

The (4-phenylbutyl)phosphonous acid, diethyl ester (5.9 g.) is added dropwise with stirring to 4.5 g. of methyl bromoacetate at a rate to maintain the temperature at 60°–70°. After an additional hour at this temperature, volatiles are removed under high vacuum leaving 6.2 g. of residual homogeneous product. This material is treated with 21 ml. of 1 N sodium hydroxide at room temperature for 30 minutes and washed with ether. The aqueous solution is acidified with 3.5 ml. of 6 N hydrochloric acid and extracted with ethyl acetate. The organic fraction is dried (MgSO4) and concentrated in vacuo to give 5.6 g. of [ethoxy(4-phenylbutyl)phosphinyl]acetic acid as a homogeneous oil. Tlc (dichloromethane/acetic acid/methanol; 8:1:1) shows a spot at $R_f$ 0.75.

(c) (+)-4,5-Dihydro-1-[[ethoxy(4-phenylbutyl)-phosphinyl]acetyl]-3-phenyl-1H-pyrazole-5-carboxylic acid A solution of 4.4 g. [ethoxy(4-phenylbutyl)-phosphinyl]acetic acid, from part (b), in 50 ml. of dry tetrahydrofuran, maintained under argon at 5°, is treated with 2.5 g. of 1,1'-carbonyldiimidazole. After stirring for one hour, the mixture is treated with 1.56 g. of triethylamine and 3.0 g. of (+)-4,5-dihydro-3-phenyl-1H-pyrazole-5-carboxylic acid, from part (a), and then the reaction mixture is allowed to stir at ambient temperature overnight. The solvent is evaporated in vacuo and the residue is dissolved in ethyl acetate and washed with 10% potassium hydrogen sulfate, water, and saturated sodium bicarbonate. The major portion of the product remained in the potassium hydrogen sulfate wash. This and the sodium bicarbonate wash are treated with 6 N hydrochloric acid to pH 1.5 and extracted with ethyl acetate to give 5.7 g. and 0.9 g. from each fraction, respectively. The combined crude product is flash chromatographed on silica gel eluting with dichloromethane/acetic acid/methanol (32:1:1) to give 4 g. of a mixture and 1.7 g. of homogeneous product. The mixture is rechromatographed under the same conditions to give another 2.2 g. of homogeneous product for a total of 3.9 g, of (+)-4,5-dihydro-1-[[ethoxy(4-phenylbutyl)-phosphinyl]acetyl]-3-phenyl-1H-pyrazole-5-carboxylic acid. Tlc (dichloromethane/acetic acid/methanol; 18:1:1) shows a spot at $R_f$ 0.30.

Anal. Calc'd. for $C_{24}H_{29}N_2O_5P \cdot 0.5H_2O$: C, 61.92; H, 6.49; N, 6.01, Found: C, 61.61; H, 6.44; N, 5.69.

(d) (+)-4,5-Dihydro-1-[[hydroxy(4-phenylbutyl)-phosphinyl]acetyl]-3-phenyl-1H-pyrazole-5-carboxylic acid A solution of 1.0 g, of the ethyl ester product from part (c) in 20 ml. of dry dichloromethane under argon at ambient temperature is treated with 0.5 g. of bromotrimethylsilane. After stirring overnight, volatiles are removed in vacuo and the residue, dissolved in 20 ml. of water containing 6 ml. of 1 N sodium hydroxide, is filtered to remove insoluble material. This solution is washed with ether, then acidified to pH 2.0 with 6 N hydrochloric acid and extracted with ethyl acetate (2×75 ml.). The organic solution is filtered rapidly through Celite and concentrated to about one-half volume. The cloudy mixture is cooled and filtered to give 0.64 g. of colorless (+)-4,5-dihydro-1-[[hydroxy(4-phenylbutyl)phosphinyl]acetyl]-3-phenyl-1H-pyrazole-5-carboxylic acid, m.p. 166°–169°; $[\alpha]_D^{20} = -52°$ (1% in methanol). Tlc (dichloromethane/acetic acid/methanol; 8:1:1) shows a spot at $R_f$ 0.25.

Anal. Calc'd. for $C_{22}H_{25}N_2O_5P$: C, 61.67; H, 5.88; N, 6.54; P, 7.22, Found: C, 61.30; H, 5.77; N, 6.56; P, 7.30.

EXAMPLES 2-37

Following the procedure of Example 1 but employing the phosphinate shown in Col. I and the dihydropyrazole shown in Col. II, one obtains the compound shown in Col. III. Removal of the ester group yields the diacid product of Col. IV.

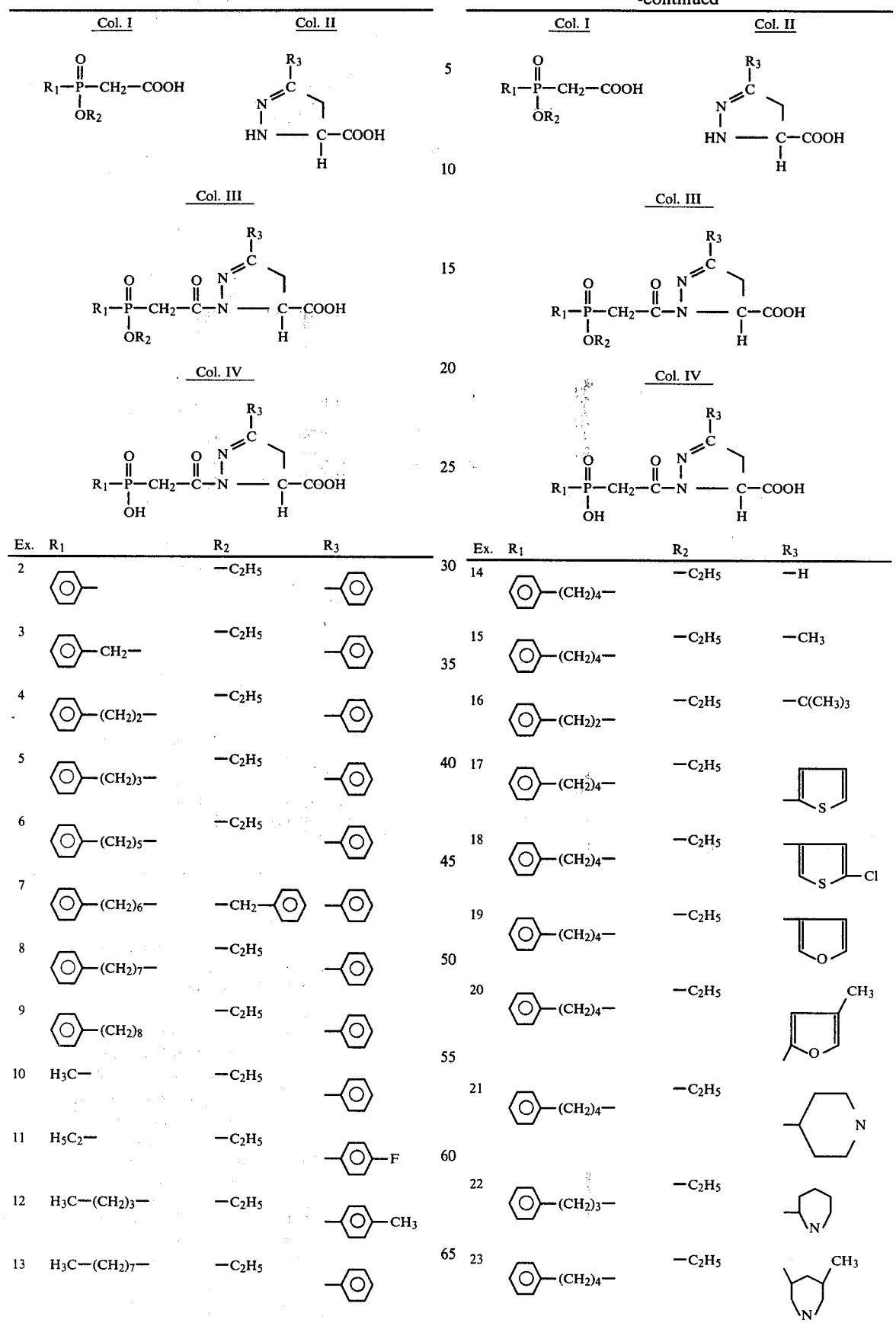

-continued

| | Col. I | Col. II |
|---|---|---|
| | $R_1-\overset{O}{\underset{OR_2}{P}}-CH_2-COOH$ | (imine-pyrazoline with R3, HN—C(H)—COOH) |

Col. III $R_1-\overset{O}{\underset{OR_2}{P}}-CH_2-\overset{O}{C}-N$ — (pyrazoline with R3) —C(H)—COOH Col. IV $R_1-\overset{O}{\underset{OH}{P}}-CH_2-\overset{O}{C}-N$ — (pyrazoline with R3) —C(H)—COOH

| Ex. | R₁ | R₂ | R₃ |
|---|---|---|---|
| 24 | C₆H₅—(CH₂)₄— | —C₂H₅ | —C₆H₄—OCH₃ |
| 25 | C₆H₅—(CH₂)₂— | —C₂H₅ | —C₆H₄—SCH₃ |
| 26 | C₆H₅—(CH₂)₃— | —C₂H₅ | —C₆H₄—OH |
| 27 | C₆H₅—(CH₂)₅— | —C₂H₅ | —C₆H₄—CF₃ |
| 28 | C₆H₅—(CH₂)₄— | —C₂H₅ | —C₆H₄—Cl |
| 29 | C₆H₅—(CH₂)₄— | —C₂H₅ | —C₆H₃(CH₃)₂ |
| 30 | C₆H₅—(CH₂)₄— | —C₂H₅ | —C₆H₂(OCH₃)₃ |
| 31 | Cl—C₆H₄—(CH₂)₄— | —C₂H₅ | —C₆H₅ |
| 32 | H₃C—C₆H₄—(CH₂)₄— | —CH₂—C₆H₅ | —C₆H₅ |
| 33 | HO—C₆H₄—(CH₂)₂— | —C₂H₅ | —(thienyl) |

-continued

| | Col. I | Col. II |
|---|---|---|
| | $R_1-\overset{O}{\underset{OR_2}{P}}-CH_2-COOH$ | (imine-pyrazoline with R3, HN—C(H)—COOH) |

Col. III $R_1-\overset{O}{\underset{OR_2}{P}}-CH_2-\overset{O}{C}-N$ — (pyrazoline with R3) —C(H)—COOH Col. IV $R_1-\overset{O}{\underset{OH}{P}}-CH_2-\overset{O}{C}-N$ — (pyrazoline with R3) —C(H)—COOH

| Ex. | R₁ | R₂ | R₃ |
|---|---|---|---|
| 34 | F—C₆H₄—CH₂— | —C₂H₅ | —(furyl) |
| 35 | H₃CO—C₆H₄—(CH₂)₃— | —C₂H₅ | —(pyridyl) |
| 36 | F₃C—C₆H₄—(CH₂)₄— | —C₂H₅ | —CH₃ |
| 37 | H₃C—C₆H₃(CH₃)—(CH₂)₄— | —C₂H₅ | —H |

EXAMPLE 38

(+)-4,5-Dihydro-1-[[hydroxy(4-phenylbutyl)phosphinyl]acetyl]-3-phenyl-1H-pyrazole-5-carboxylic acid, (2,2-dimethyl-1-oxopropoxy)methyl ester (a)
(+)-4,5-Dihydro-1-[[ethoxy(4-phenylbutyl)phosphinyl]acetyl]-3-phenyl-1H-pyrazole-5-carboxylic acid, (2,2-dimethyl-1-oxopropoxy)methyl ester A solution of 1.6 g. of (+)-4,5-dihydro-1-[[ethoxy(4-phenylbutyl)phosphinyl]acetyl]-3-phenyl-1H-pyrazole-5-carboxylic acid, from Example 1(c), in 25 ml. of dry dimethylformamide under argon at ambient temperature is treated with 0.7 g. of triethylamine and 0.54 g. of chloromethyl pivalate. After stirring overnight at ambient temperature, additional triethylamine (0.13 g.) and chloromethyl pivalate (0.12 g.) are added and stirring is continued for 60 hours. The solution is diluted with ethyl acetate and washed with water (2×), potassium hydrogen sulfate, water and saturated brine. The organic solution is dried (MgSO₄) and concentrated in vacuo to give 2.21 g. of crude product. Flash chromatography on silica gel eluting with acetone/hexane (2:1) gives 1.55 g. of homogeneous (+)-4,5-dihydro-1-[[ethoxy(4-phenylbutyl)phosphinyl]acetyl]-3-phenyl-1H-pyrazole-5-carboxylic acid, (2,2-dimethyl-1-oxopropoxy)methyl ester. Tlc acetone/hexane; 2:1) shows a spot at $R_f$ 0.30.

Anal. calc'd. for $C_{30}H_{39}N_2O_7P \cdot 0.5\ H_2O$: C, 62.16; H, 6.95; N, 4.83, Found: C, 62.14; H, 6.83; N, 4.65.

(b)

(+)-4,5-Dihydro-1-[[hydroxy(4-phenylbutyl)phosphinyl]acetyl]-3-phenyl-1H-pyrazole-5-carboxylic acid, (2,2-dimethyl-1-oxopropoxy)methyl ester A solution of 1.55 g. of the diester product from part (a) in 40 ml. of dry dichloromethane under argon at ambient temperature is treated with 0.62 g. of bromotrimethylsilane and stirred overnight. Volatiles are removed in vacuo and the residue, dissolved in ethyl acetate, is washed with 5% sodium dihydrogen phosphate, water, and saturated brine. The organic solution is dried ($MgSO_4$) and concentrated in vacuo to give 1.1 g. of colorless solid, (+)-4,5-dihydro-1-[[hydroxy(4-phenylbutyl)phosphinyl]acetyl]-3-phenyl-1H-pyrazole-5-carboxylic acid, (2,2-dimethyl-1-oxopropoxy)methyl ester; m.p. 145°–147°. Tlc (dichloromethane/acetic acid/methanol; 18:1:1) shows a spot at $R_f$ 0.30.

Anal. calc'd. for $C_{28}H_{35}N_2O_7P \cdot 0.25\ H_2O$: C, 61.47; H, 6.54; N, 5.12; P, 5.66, Found: C, 61.31; H, 6.53; N, 5.05; P, 5.7.

EXAMPLE 39

(+)-4,5-Dihydro-1-[[hydroxy(4-phenylbutyl)phosphinyl]acetyl]-3-phenyl-1H-pyrazole-5-carboxylic acid, 1-(2,2-dimethyl-1-oxopropoxy)-2-ethoxy-2-oxoethyl ester (a) Ethyl 2-chloro-2-pivaloyloxyacetate Following the general method of Ulich and Adams [J. Amer. Chem. Soc., Vol. 43, p 660 (1921)], a pinch of freshly fused zinc chloride is added to a mixture of 4.0 g. of anhydrous ethyl glyoxalate and 4.72 g. of pivaloyl chloride. The mixture is heated under argon at 80° for 2 hours, then distilled in vacuo to give 4.7 g. of ethyl 2-chloro-2-pivaloyloxyacetate, b.p. 50°/0.03 mm of Hg.

(b)

(+)-4,5-Dihydro-1-[[ethoxy(4-phenylbutyl)phosphinyl]acetyl]-3-phenyl-1H-pyrazole-5-carboxylic acid, 1-(2,2-dimethyl-1-oxopropoxy)-2-ethoxy-2-oxoethyl ester A solution of 2.0 g. of (+)-4,5-dihydro-1-[[ethoxy(4-phenylbutyl)phosphinyl]acetyl]-3-phenyl-1H-pyrazole-5-carboxylic acid, from Example 1(c), in 30 ml. of dry dimethylformamide under argon at room temperature is treated with 1.2 g. of ethyl 2-chloro-2-pivaloyloxyacetate, from part (a), and 0.58 g. of anhydrous potassium fluoride. After stirring for 48 hours the mixture is diluted with ethyl acetate and washed with water (3×). The organic fraction is dried ($MgSO_4$) and concentrated in vacuo to give crude product. Flash chromatography on silica gel and elution with acetone/hexane (2:1) gives homogeneous (+)-4,5-dihydro-1-[[ethoxy(4-phenylbutyl)phosphinyl]acetyl]-3-phenyl-1H-pyrazole-5-carboxylic acid, 1-(2,2-dimethyl-1-oxopropoxy)-2-ethoxy-2-oxoethyl ester as an oil.

(c)

(+)-4,5-Dihydro-1-[[hydroxy(4-phenylbutyl)phosphinyl]acetyl]-3-phenyl-1H-pyrazole-5-carboxylic acid, 1-(2,2-dimethyl-1-oxopropoxy)-2-ethoxy-2-oxoethyl ester A solution of 2.0 g of the diester product from part (b) in 25 ml. of dry dichloromethane under argon is treated at ambient temperature with 0.6 g. of bromotrimethylsilane. After stirring overnight, the volatiles are removed in vacuo and the residue, dissolved in ethyl acetate, is washed with 5% sodium dihydrogen phosphate, water and saturated brine. The organic fraction is dried ($MgSO_4$) and concentrated in vacuo. The residue is triturated with acetonitrile or purified by flash chromatography to give (+)-4,5-dihydro-1-[[hydroxy(4-phenylbutyl)phosphinyl]acetyl]-3-phenyl-1H-pyrazole-5-carboxylic acid, 1-(2,2-dimethyl-1-oxopropoxy)-2-ethoxy-2-oxoethyl ester.

EXAMPLES 40–47

Following the procedure of Examples 38 and 39 but employing the alkylating agent shown in Col. I for the chloromethyl pivalate in Example 38 or for the ethyl 2-chloro-2-pivaloyloxyacetate in Example 39 one obtains the product shown in Col. II.

Col. I

Col. II

| Ex. | X   | R₄           | R₅     |
|-----|-----|--------------|--------|
| 40  | Br— | —H           | —CH₃   |
| 41  | Cl— | —CH₃         |  |
| 42  | Cl— | —CH₃         | —CH₃   |
| 43  | Cl— | —CO₂C₂H₅     | —CH₃   |
| 44  | Cl— | —CO₂C₂H₅     |        |
| 45  | Cl— | —H           | —OCH₃  |
| 46  | —Cl | —CH₂—CH₂—    |        |
| 47  | —Br |              |        |

Similarly, by employing the monoester compounds shown in Col. III of Examples 2 to 37 within the procedure of Examples 38 to 47, other compounds within the scope of the invention are obtained.

EXAMPLE 48

(+)-4,5-Dihydro-1-[[[(2,2-dimethyl-1-oxopropoxy)methoxy](4-phenylbutyl)phosphinyl]acetyl]-3-phenyl-1H-pyrazole-5-carboxylic acid

(a)
(+)-4,5-Dihydro-3-phenyl-1H-pyrazole-5-carboxylic acid, phenylmethyl ester, hydrochloride (1:1)

20 g. of (+)-4,5-Dihydro-3-phenyl-1H-pyrazole-5-carboxylic acid is added at room temperature to a solution of 25 g. of thionyl chloride in 150 ml. of benzyl alcohol (prepared by adding the thionyl chloride to the benzyl alcohol at −5°) and allowed to stir for 48 hours. Hydrochloric acid is removed in vacuo and the remaining solution is poured into 250 ml. of anhydrous ether. The separated product is collected, washed with fresh ether, and dried to give (+)-4,5-dihydro-3-phenyl-1H-pyrazole-5-carboxylic acid, phenylmethyl ester, hydrochloride (1:1).

(b) [Hydroxy(4-phenylbutyl)phosphinyl]acetic acid

[Ethoxy(4-phenylbutyl)phosphinyl]acetic acid from Example 1(b), is further saponified by heating with excess sodium hydroxide, acidification and recrystallization of the product from tetrahydrofuran/hexane to obtain [hydroxy(4-phenylbutyl)phosphinyl]acetic acid; m.p. 109.5°–110°.

Anal. calc'd. for $C_{12}H_{17}O_4P$: C, 56.24; H, 6.69; P, 12.09, Found: C, 56.11; H, 6.42; P, 12.1.

(c)
(+)-4,5-Dihydro-1-[[hydroxy(4-phenylbutyl)phosphinyl]acetyl]-3-phenyl-1H-pyrazole-5-carboxylic acid, phenylmethyl ester A solution of 10 g. of [hydroxy(4-phenylbutyl)phosphinyl]acetic acid, from part (b), in 40 ml. of dry dichloromethane containing 0.2 ml. of dimethylformamide is heated to reflux temperature. Thionyl chloride (5.1 g.) is added dropwise while maintaining the temperature at reflux. After an additional 30 minutes heating, the solution is cooled to 5° and a solution of 11.6 g. of (+)-4,5-dihydro-3-phenyl-1H-pyrazole-5-carboxylic acid, phenylmethyl ester, hydrochloride (1:1), from part (a), in 50 ml. of dichloromethane is added at once, followed by dropwise addition of 11.9 g. of triethylamine while the temperature is maintained at 5°–10° with cooling. After stirring overnight at ambient temperature, the mixture is washed three times with aqueous hydrochloric acid (1.5 N) and three times with water. The organic solution is dried ($MgSO_4$) and concentrated in vacuo to give (+)-4,5-dihydro-1-[[hydroxy(4-phenylbutyl)phosphinyl]acetyl]-3-phenyl-1H-pyrazole-5-carboxylic acid, phenylmethyl ester which can be crystallized from acetone.

(d)
(+)-4,5-Dihydro-1-[[[(2,2-dimethyl-1-oxopropoxy)methoxy](4-phenylbutyl)phosphinyl]acetyl]-3-phenyl-1H-pyrazole-5-carboxylic acid, phenylmethyl ester A solution of 4.0 g. of the benzyl ester product from part (c) dissolved in 40 ml. of dry dimethylformamide under argon is treated at ambient temperature with 1.5 g. of chloromethyl pivalate and 1.8 g. of triethylamine. After stirring overnight, the solution is diluted with ethyl acetate and washed with 10% potassium dihydrogen sulfate, water, and saturated brine. The organic solution is dried ($MgSO_4$) and concentrated in vacuo to give the crude product. Flash chromatography on silica gel and elution with ethyl acetate/dichloromethane (1:1) gives homogeneous (+)-4,5-dihydro-1-[[[(2,2-dimethyl-1-oxopropoxy)methoxy](4-phenylbutyl)phosphinyl]acetyl]-3-phenyl-1H-pyrazole-5-carboxylic acid, phenylmethyl ester as an oil.

(e)
(+)-4,5-Dihydro-1-[[[(2,2-dimethyl-1-oxopropoxy)methoxy](4-phenylbutyl)phosphinyl]acetyl]-3-phenyl-1H-pyrazole-5-carboxylic acid The diester product from part (d) (2.0 g.) is dissolved in 50 ml. of methanol containing 0.5 g. of 5% palladium on carbon catalyst and hydrogenated at 50 psi on a Parr apparatus until cessation of hydrogen uptake (2–4 hours). The catalyst is filtered off and the filtrate is concentrated in vacuo. The residue is triturated with acetonitrile or purified by flash chromatography to give (+)-4,5-dihydro-1-[[[(2,2-dimethyl-1-oxopropoxy)methoxy] (4-phenylbutyl)phosphinyl]acetyl]-3-phenyl-1H-pyrazole-5-carboxylic acid.

EXAMPLES 49–57

Folowing the procedure of Example 48 but employing the alkylating agent shown in Col. I for the chloromethyl pivalate one obtains the product shown in Col. II.

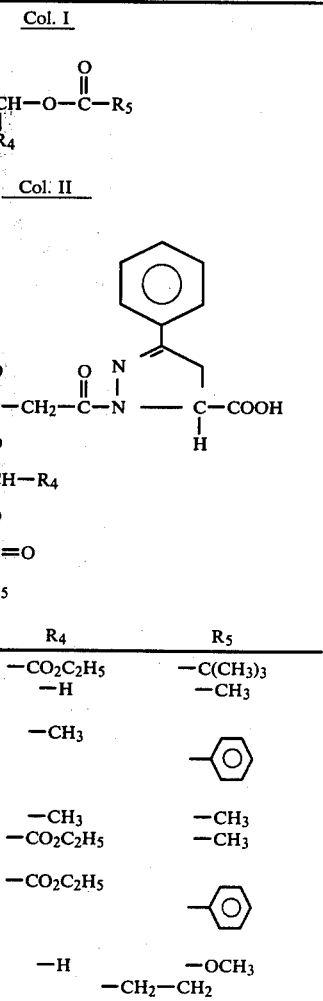

| Ex. | X | $R_4$ | $R_5$ |
|---|---|---|---|
| 49 | Cl— | —$CO_2C_2H_5$ | —$C(CH_3)_3$ |
| 50 | Br— | —H | —$CH_3$ |
| 51 | Cl— | —$CH_3$ | —C₆H₅ |
| 52 | Cl— | —$CH_3$ | —$CH_3$ |
| 53 | Cl— | —$CO_2C_2H_5$ | —$CH_3$ |
| 54 | Cl— | —$CO_2C_2H_5$ | —C₆H₅ |
| 55 | Cl— | —H | —$OCH_3$ |
| 56 | Cl— |  | —$CH_2$—$CH_2$ |

-continued

Col. I

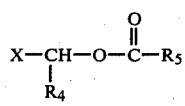

Col. II

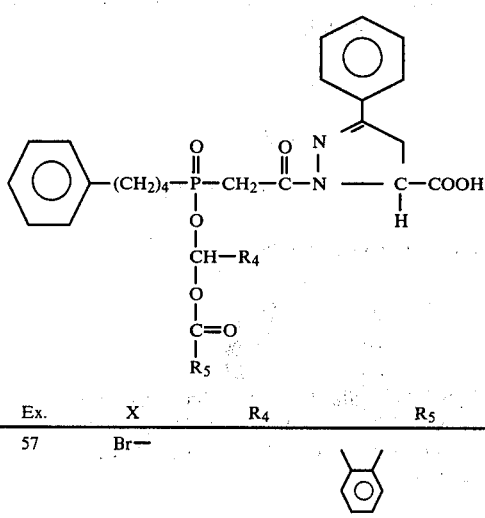

| Ex. | X | $R_4$ | $R_5$ |
|---|---|---|---|
| 57 | Br— | | |

Similarly, by employing the benzyl ester of the dihydropyrazoles shown in Col. II of Examples 2 to 37 and the acid obtained by saponification of the esters shown in Col. I of Examples 2 to 37 within the procedures of Examples 48 to 57, other compounds within the scope of this invention are obtained.

EXAMPLE 58

(+)-4,5-Dihydro-1-[[hydroxy(4-phenylbutyl)-phosphinyl]acetyl]-3-phenyl-1H-pyrazole-5-carboxylic acid, disodium salt An aqueous solution containing (+)-4,5-dihydro-1-[[hydroxy(4-phenylbutyl)phosphinyl]acetyl]-3-phenyl-1H-pyrazole-5-carboxylic acid, from Example 1, is treated with 2 equivalents of sodium bicarbonate solution and lyophilized to yield (+)-4,5-dihydro-1-[[hydroxy(4-phenylbutyl)phosphinyl]acetyl]-3-phenyl-1H-pyrazole-5-carboxylic acid, disodium salt.

In an analogous manner the corresponding dipotassium and dilithium salt can be obtained.

Similarly, the products of Examples 2 to 37 can be treated to obtain the corresponding disodium salt and the products of Examples 38 to 57 can be treated to obtain the corresponding monosodium salt.

EXAMPLE 59

1000 tablets each containing the following ingredients:

| | |
|---|---|
| (+)-4,5-Dihydro-1-[[hydroxy(4-phenylbutyl)phosphinyl]acetyl]-3-phenyl-1H-pyrazole-5-carboxylic acid | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the (+)-4,5-dihydro-1-[[hydroxy(4-phenylbutyl)phosphinyl]acetyl]-3-phenyl-1H-pyrazole-5-carboxylic acid and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 58 can be prepared.

EXAMPLE 60

Two piece #1 gelatin capsules each containing 100 mg. of (+)-4,5-dihydro-1-[[hydroxy(4-phenylbutyl)-phosphinyl]acetyl]-3-phenyl-1H-pyrazole-5-carboxylic acid, (2,2-dimethyl-1-oxopropoxy)methyl ester are filled with a mixture of the following ingredients:

| | |
|---|---|
| (+)-4,5-Dihydro-1-[[hydroxy(4-phenylbutyl)phosphinyl]acetyl]-3-phenyl-1H-pyrazole-5-carboxylic acid, (2,2-dimethyl-1-oxopropoxy)methyl ester | 100 mg. |
| Magnesium stearate | 7 mg. |
| Lactose | 193 mg. |
| | 300 mg. |

In a similar manner, capsules containing 100 mg. of the product of any of Examples 1 to 37 and 39 to 58 can be prepared.

EXAMPLE 61

1000 tablets each containing the following ingredients:

| | |
|---|---|
| (+)-4,5-Dihydro-1[[[(2,2-dimethyl-1-oxopropoxy)methoxy](4-phenylbutyl)phosphinyl]acetyl]-3-phenyl-1H-pyrazole-5-carboxylic acid | 100 mg. |
| Avicel | 100 mg. |
| Hydrochlorothiazide | 12.5 mg. |
| Lactose | 113 mg. |
| Corn starch | 17.5 mg. |
| Stearic acid | 7 mg. |
| | 350 mg. | are prepared from sufficient bulk quantities by slugging the (+)-4,5-dihydro-1-[[[(2-dimethyl-1-oxopropoxy)-methoxy](4-phenylbutyl)phosphinyl]acetyl]-3-phenyl-1H-pyrazole-5-carboxylic acid, Avicel and a portion of the stearic acid. The slugs are ground and passed through a #2 screen, then mixed with the hydrochlorothiazide, lactose, corn starch, and remainder of the stearic acid. The mixture is compressed into 350 mg. capsule shaped tablets in a tablet press. The tablets are scored for dividing in half.

In a similar manner, tablets can be prepared containing 100 mg. of the prodcut of any of Examples 1 to 47 and 49 to 58.

What is claimed is:

1. A compound of the formula:

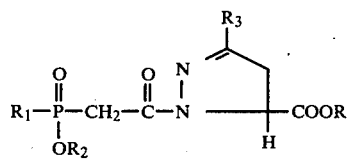

or a basic, physiologically acceptable salt thereof wherein

R and R$_2$ are independently selected from the group consisting of hydrogen, lower alkyl of 1 to 4 carbons, benzyl, and

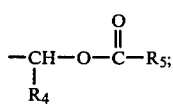

R$_3$ is hydrogen, alkyl,

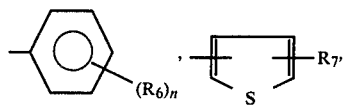

R$_1$ is alkyl or

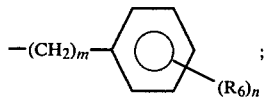

R$_4$ is hydrogen, lower alkyl of 1 to 4 carbons, phenyl, or

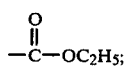

R$_5$ is hydrogen, lower alkyl of 1 to 4 carbons, lower alkoxy of 1 to 4 carbons, phenyl, or R$_4$ and R$_5$ taken together are —(CH$_2$)$_2$—, —(CH$_2$)$_3$—, —CH=CH—, or

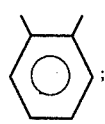

R$_6$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

n is one, two or three provided that n is two or three only if R$_6$ is hydrogen, methyl, methoxy, chloro, or fluoro;

R$_7$ is hydrogen, lower alkyl of 1 to 4 carbons, chloro, bromo, or fluoro; and m is zero or an integer from 1 to 8.

2. A compound of claim 1 wherein:

R and R$_2$ are independently selected from the group consisting of hydrogen, alkali metal, and

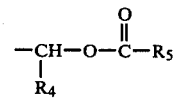

provided that at least one of R and R$_2$ is hydrogen or alkali metal;

R$_3$ is

R$_4$ is hydrogen, methyl, or

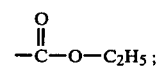

R$_5$ is lower alkyl of 1 to 4 carbons or phenyl;

R$_6$ is hydrogen, methyl, methoxy, methylthio, trifluoromethyl, chloro, bromo, fluoro, or hydroxy; and R$_1$ is alkyl or

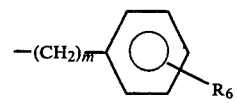

wherein R$_6$ is as defined above and m is an integer from 2 to 6.

3. A compound of claim 2 wherein

R and R$_2$ are independently selected from the group consisting of hydrogen, alkali metal,

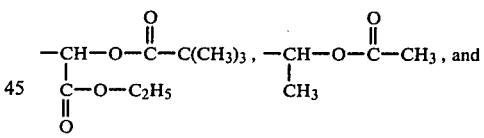

provided that at least one of R and R$_2$ is hydrogen or alkali metal;

R$_3$ is phenyl; and

R$_1$ is

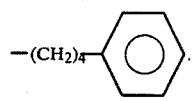

4. The compound of claim 3 wherein R and R$_2$ are hydrogen.

5. The compound of claim 4, (+)-4,5-dihydro-1-[[hydroxy(4-phenylbutyl)phosphinyl]-acetyl]-3-phenyl-1H-pyrazole-5-carboxylic acid.

6. The compound of claim 3 wherein R$_2$ is hydrogen and R is

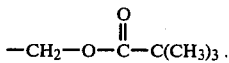

7. The compound of claim 6, (+)-4,5-dihydro-1-[[hydroxy(4-phenylbutyl)phosphinyl]-acetyl]-3-phenyl-1H-pyrazole-5-carboxylic acid, (2,2-dimethyl-1-oxopropoxy)methyl ester.

8. The compound of claim 3 wherein R is hydrogen and $R_2$ is

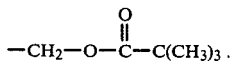

9. The compound of claim 8, (+)-4,5-dihydro-1-[[[(2,2-dimethyl-1-oxopropoxy)methoxy](4-phenylbutyl)phosphinyl]acetyl]-3-phenyl-1H-pyrazole-5-carboxylic acid.

10. A composition useful for treating hypertension comprising a pharmaceutically acceptable carrier and an effective amount of a hypotensive agent or pharmaceutically acceptable salt thereof of the formula

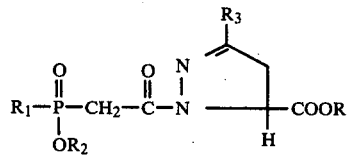

wherein R, $R_1$, $R_2$ and $R_3$ are as defined in claim 1.

11. The composition of claim 10 also including a diuretic.

12. The method of alleviating hypertension in a mammalian specie suffering from hypertension which comprises administering an effective amount of the composition of claim 10.

* * * * *